United States Patent [19]

Thamm et al.

[11] Patent Number: 5,527,777
[45] Date of Patent: Jun. 18, 1996

[54] PEPTIDE COMPOUNDS, IN PARTICULAR LHRH-ANTAGONISTS

[75] Inventors: Paul Thamm, Taufkirchen; Alessandro Lobbia, Berlin; Thomas Brumby, Berlin; Johann Mulzer, Berlin; Fridtjog Schröder, Berlin; Ursula Habenicht, Berlin, all of Germany

[73] Assignee: Schering Aktiengesellschaft, Berlin, Germany

[21] Appl. No.: 142,429

[22] PCT Filed: May 22, 1992

[86] PCT No.: PCT/DE92/00427

§ 371 Date: May 4, 1994

§ 102(e) Date: May 4, 1994

[87] PCT Pub. No.: WO92/20711

PCT Pub. Date: Nov. 26, 1992

[30] Foreign Application Priority Data

May 24, 1991 [DE] Germany .................. 41 17 507.7

[51] Int. Cl.$^6$ .................. A61K 38/00; A61K 38/02; C07K 5/00; C07K 7/00
[52] U.S. Cl. .................. 514/15; 530/328; 530/313
[58] Field of Search .................. 514/15–16; 530/313, 530/328, 329

[56] References Cited

U.S. PATENT DOCUMENTS 4,667,014  5/1987  Nestor, Jr. et al. .................. 530/313

FOREIGN PATENT DOCUMENTS 0277829  8/1988  European Pat. Off. .
0299402  1/1989  European Pat. Off. .......... C07K 7/20
0410260  1/1991  European Pat. Off. .
89/01944  3/1989  WIPO .

OTHER PUBLICATIONS

Liu et al., *Science in China* (Series B), vol. 34, No. 2, pp. 201–208 (Feb. 1991).
Lane, "Sodium Cyanoborohydride—A Highly Selective Reducing Agent for Organic Functional Groups," *Synthesis*, No. 3, pp. 135–146 (Mar. 1975).
Barrass et al., "The Formation of Cyclic Lactams from Derivatives of Basic Amino–acids," J. Chem. Soc., Part IV, pp. 4830–4834 (1957).

Primary Examiner—Christina Y. Chan
Assistant Examiner—A. M. Davenport
Attorney, Agent, or Firm—Millen, White, Zelano & Branigan

[57] ABSTRACT

The invention concerns LHRH antagonists of the general formula (I), $$X\text{-}X_1\text{-}X_2\text{-}X_3\text{-}L\text{-}Ser\text{-}L\text{-}Tyr\text{-}X_6\text{-}L\text{-}Leu\text{-}X_8\text{-}L\text{-}Pro\text{-}X_{10} \qquad (I)$$

The invention concerns LHRH antagonists of the general formula (I), in which X is an acyl group, $X_1$ is a D-Nal, $X_2$ is D-(4-Cl)-Phe, $X_3$ is D-(3)-Pal, $X_6$ is D-Cit or D-Neu, $X_8$ is L-Arg or L-Neu, at least one of the groups $X_6$ and $X_8$ being a Neu, and $X_{10}$ is D-Ala-NH$_2$, Neu being a group of formula (II), (IV), (IX) or (X), wherein W is one of the group (a)–(d). The invention includes drugs containing a compound of formula (I), plus the usual auxiliaries and carriers. These drugs are suitable for use in cases of carcinoma of the prostate and in endometriosis, as well as for fertility control.

8 Claims, No Drawings

PEPTIDE COMPOUNDS, IN PARTICULAR LHRH-ANTAGONISTS

This application is a 371 of international application PCT/DE92/00427 filed May 22, 1992.

The invention relates to peptide compounds, in particular LHRH antagonists, their production and use as medicines, further, amino acids with nitrogen in the side chain and their production. (LHRH=luteinizing hormone-releasing hormone)

The luteinizing hormone-releasing hormone is produced in mammals in the hypothalamus. In the pituitary gland, it stimulates the release of luteinizing hormones (LH) and follicle-stimulating hormones (FSH). The latter in turn control the production of androgens and estrogens in the reproductive organs.

By administration of single doses of LHRH or synthetic agonists, increased production of steroid hormones (e.g. testosterone) can be achieved. Long term administration leads, however, to a reduction of hormone production. This effect has been used for some time for treating hormone-dependent tumors (prostate cancer).

The accompanying effect of this treatment is the initial stimulation of the hormones to be suppressed. This effect, which leads to transient tumor growth (tumor flare-up) in hormone-dependent tumors, can be avoided by using LHRH antagonists. Karten et al. (Endocrine Rev. 7, 44, 1986) and Dutta (Drugs of the Future 13, 761, 1988) have described the development of LHRH antagonists.

But effective LHRH antagonists, which have basic amino acids in 6- and 8-position, release undesirably high amounts of histamine. Various efforts have been made to reduce the release of histamine. European publication EP-OS 097 031 describes arginine derivatives in 6-position. European publication EP-OS 0 277 829 represents basic amino acid derivatives in 6- and 8-position. European publication EP-OS 0 299 402 discloses the combination of citrulline in 6-position with arginine in 8-position, in which quite little histamine is released.

It has now been found, surprisingly, that by exchange of 6- and 8-position for lysine derivatives, which are substituted on omega-nitrogen, an increase in the effect of reducing the release of histamine can be achieved.

According to the invention, peptide compounds of formula I are claimed,

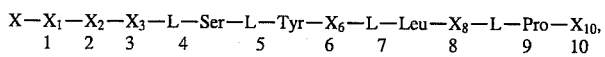

in which

X stands for a naphthoyl, naphthylacetyl, naphthylpropionyl, benzoyl group or an acyl group with 1–7 carbon atoms, $X_1$ stands for D-(1)-Nal, D-(2)-Nal, D-Phe, D-(4-Y)-Phe, D-(3)-Qal or a direct bond, in which Y is an F, Br or Cl group, $X_2$ stands for D-Phe, D-(4-Y)-Phe or a direct bond, in which Y has the previously mentioned meaning, $X_3$ stands for D-Trp, D-Phe, D-(4-Y)-Phe, D-(3)-Pal, D-(2)-Nal or a direct bond, in which Y has the meaning already mentioned for $X_1$, $X_6$ stands for D-Cit, D-Hci, D-Orn, D-Lys or D-Neu, $X_8$ stands for L-Orn, L-Arg, L-Lys or L-Neu, and at least one of radicals $X_6$ and $X_8$ is an Neu, and $X_{10}$ stands for D-Ala-$NH_2$, Gly-$NH_2$, azaglycine, -NHEt or -NH(CO)$NH_2$, and Neu represents a group of formula II,

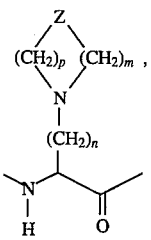

in which Z stands for a group $>CH_2$, $>C=O$, $>CH(OH)$, $>O$, $>S$, $>S=O$, $>SO_2$, $>NR_1$ oder $>N(CO)R_2$ $R_1$ is a hydrogen atom or a $C_1$-$C_4$ alkyl group and $R_2$ is a hydrogen atom, a $C_1$-$C_4$ alkyl group or an amino group, n stands for 1 to 8, m stands for 1 to 3, if Z is one of radicals —($CH_2$)—, —CO— or —CH(OH)—, or m stands for 2 and 3, if Z are the radicals —O—, —S—, —SO—, —$SO_2$—, —$NR_1$— or —N(CO)$R_2$—, p stands for 1 to 3, or Neu represents a group of formula III,

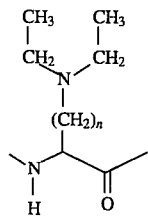

in which n stands for 1 to 8, or Neu represents a group of formula IV,

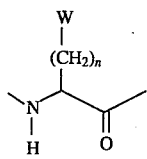

in which W represents one of radicals

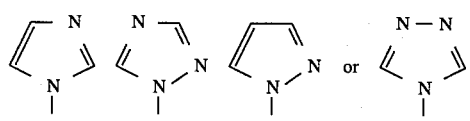

and n stands for a number from 1 to 8.

The text comprises some abbreviations, whose meaning is explained below. There, the rules set by the IUPAC-IUB Commission for biochemical nomenclature are followed (Biochemistry 11: 1726 (1972 and Biochem. J. 219: 345 (1984)).

In addition, the following abbreviations and their combinations are used:

| | |
|---|---|
| Ape | 2-amino-pentanoic acid |
| Ahx | 2-amino-hexanoic acid |
| Ahp | 2-amino-heptanoic acid |
| Aoc | 2-amino-octanoic acid |
| Ano | 2-amino-nonanoic acid |
| Mor | morpholin-4-yl- |
| Pip | piperidin-1-yl- |
| Pyr | pyrrolidin-1-yl- |
| Tht | tetrahydro-1,4-thiazin-4-yl- |
| Mpz | 4-methyl-piperazin-1-yl- |
| Pon | 4-piperidon-1-yl- |
| Hpi | 4-hydroxy-piperidin-1-yl- |
| Aps | 4-aza-pentamethylenesulfon-4-yl- |
| (1)-Nal | 3-(naphth-1-yl)-alanine |
| (2)-Nal | 3-(naphth-2-yl)-alanine |
| (3)-Pal | 3-(3-pyridyl)-alanine |
| (3)-Qal | 3-(quinol-3-yl)-alanine |
| Hci | homocitrulline |
| 1Im | imidazol-1-yl- |
| 4Tr | 1,3,4-triazol-4-yl- |
| 1Tr | 1,3,4-triazol-1-yl- |
| 1Py | pyrazol-1-yl- |
| Cpz | 4-carbamoyl-piperazin-1-yl- |
| Cpa | 4-chloro-phenylalanine |

Thus, e.g., Aoc(Mor)=6-morpholin-4-yl-2-amino-octanoic acid, Ape(Pip)=5-piperidin-4-yl-2-amino-pentanoic acid and Ahx(1Im)=6-(imidazol-1-yl)-2-aminohexanoic acid.

The peptides are represented in an abbreviated form, in which only the amino acids changed in comparison to LHRH and their position are indicated. Thus, e.g., pyroGlu$^1$-His$^2$-Trp$^3$-Ser$^4$-Tyr$^5$-D-Nal$^6$-Leu$^7$-Arg$^8$-Pro$^9$-D-Ala$^{10}$-NH$_2$ becomes [D-Nal$^6$,D-Ala$^{10}$]LHRH.

The alkyl groups mentioned in the text are straight or branched and mean methyl, ethyl, propyl, isopropyl, n-butyl, sec-butyl, isobutyl, tert-butyl, pentyl, isopentyl, neopentyl, hexyl, isohexyl, heptyl, isoheptyl.

The advantages of the peptide compounds according to the invention consist in that the pharmacological action of the peptide compounds is very great and the side effects in the form of release of histamine are kept slight.

Advantageous are peptide compounds, in which Neu stands for a radical of formula IX

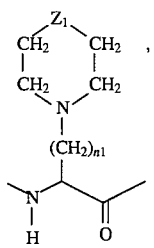
(IX)

in which $Z_1$ stands for a group
>CH$_2$, >CH(OH), >O, >S, >SO$_2$, >NCH$_3$ or a direct bond, and $n_1$ stands for 3 to 6.

Preferred are peptide compounds, in which Neu stands for a group of formula X,

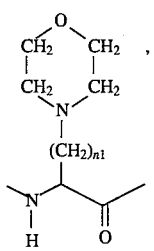
(X)

in which $n_1$ stands for 3 to 6,

More preferred are peptide compounds, in which Neu stands for the radical

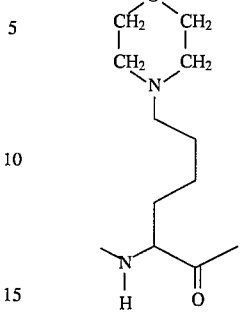

Most preferred are peptide compounds, in which Neu stands for $X_6$ or $X_8$.

Another advantageous embodiment consists in that Neu stands for formula XIII.

(XIII)

Another advantageous embodiment comprises peptide compounds, in which Neu stands for formula XIV

(XIV)

In addition to H- and J-positions, the other variable positions can also be changed. Thus, peptide compounds are preferred, in which X stands for an ethanoyl group,
$X_1$ stands for D-Nal,
$X_2$ stands for D-Cpa,
$X_3$ stands for D-Pal and
$X_{10}$ stands for D-Ala-NH$_2$.

Other preferred embodiments have, in $X_6$- and/or $X_8$-position, at least one of the following radicals: Ahx(Hpi), Ahx(Aps), Ahx(Mpz), Aoc(Mor), Ahx(1Py), Ape(Mor), Ape(Pyr) or Ape(Tht).

The most preferred peptide compound is
Ac-D-Nal-D-Cpa-D-Pal-Ser-Tyr-D-Cit-Leu-Ahx(Mor)-Pro-D-Ala-NH$_2$.

Further, the invention also comprises amino acid derivatives that occur as structural elements in the peptide compounds according to the invention.

The amino acid derivatives belong to a group of general formula XVII $$\begin{array}{c} W \\ | \\ (CH_2)_n \\ R_3 \diagdown N \diagup \diagdown R_4, \\ | \quad \| \\ R_{3'} \quad O \end{array}$$ (XVII)

in which W represents the radical $$\begin{array}{c} Z \\ \diagup \diagdown \\ (CH_2)_p \quad (CH_2)_m \\ \diagdown \diagup \\ N \\ | \end{array}$$

and

Z stands for a group
>CH$_2$, >C=O, >CH(OH), >O, >S, >S=O, >SO$_2$, >NR$_1$ oder >N(CO)R$_2$ R$_1$ is a hydrogen atom or a C$_1$-C$_4$ alkyl group, R$_2$ is a hydrogen atom, a C$_1$-C$_4$ alkyl group or an amino group, n stands for 1 to 8, m stands for 1 to 3, if Z is one of radicals —(CH$_2$)—, —CO— or —CH(OH)—, or m stands for 2 and 3, if Z are the radicals —O—, —S—, —SO—, —SO$_2$—, —NR$_1$— or —N(CO)R$_2$—, p stands for 1 to 3, R$_3$ stands for H, a protective group or a carbonyl group as part of a peptide bond of a peptide chain, R$_{3'}$ stands for H or C$_1$-C$_3$ alkyl, R$_4$ stands for O—R$_{4'}$ or an amino group as part of a peptide bond of a peptide chain, R$_{4'}$ stands for H or for a protective group or in which W stands for one of the radicals $$\begin{array}{cccc} \diagup^N \diagdown & N \diagdown & \diagup^N \diagdown & N - N \\ \Big\langle \quad \Big\rangle & \Big\langle \quad \diagdown_N & \Big\langle \quad \diagup^N & \Big\langle \quad \Big\rangle \\ N & N & N & N \\ | & | & | & | \end{array}$$ or oder and R$_3$, R$_{3'}$ and R$_4$ have the previously mentioned meanings.

Protective groups are described in Houben-Weyl (1974) Georg Thieme Verlag, 4th Edition. The list of protective groups in the bibliography is part of the disclosure.

Preferred are amino acid derivatives with general formula XVIII, $$\begin{array}{c} Z_1 \\ \diagup \diagdown \\ CH_2 \quad CH_2 \\ | \quad | \\ CH_2 \quad CH_2 \\ \diagdown N \diagup \\ | \\ (CH_2)_{n1} \\ R_3 \diagdown N \diagup \diagdown R_4 \\ | \quad \| \\ H \quad O \end{array}$$ (XVIII)

in which

Z$_1$ stands for a group
>CH$_2$, >CH(OH), >O, >S, >SO$_2$, >NCH$_3$ or a direct bond, and n$_1$ stands for 3 to 6, R$_3$ and R$_4$ have the meanings already mentioned.

More preferred are amino acid derivatives with general formula XIX, $$\begin{array}{c} O \\ \diagup \diagdown \\ CH_2 \quad CH_2 \\ | \quad | \\ CH_2 \quad CH_2 \\ \diagdown N \diagup \\ | \\ (CH_2)_{n1} \\ R_3 \diagdown N \diagup \diagdown R_4 \\ | \quad \| \\ H \quad O \end{array}$$ (XIX)

in which n$_1$ stands for 3 to 6,

R$_3$ and R$_4$ have the meanings already mentioned.

Most preferred are amino acid derivatives that have formula XX, and radicals R$_3$ and R$_4$ have the previously mentioned meanings.

$$\begin{array}{c} O \\ \diagup \diagdown \\ CH_2 \quad CH_2 \\ | \quad | \\ CH_2 \quad CH_2 \\ \diagdown N \diagup \\ | \\ (CH_2)_4 \\ R_3 \diagdown N \diagup \diagdown R_4 \\ | \quad \| \\ H \quad O \end{array}$$ (XX)

Other embodiments consist in amino acid derivatives according to the invention with general formula XXII $$\begin{array}{c} \diagup^N \diagdown \\ \Big\langle \quad \Big\rangle \\ N \\ | \\ (CH_2)_4 \\ R_3 \diagdown N \diagup \diagdown R_4 \\ | \quad \| \\ H \quad O \end{array}$$ (XXII)

and radicals R$_3$ and R$_4$ have the previously mentioned meanings. Use of the peptide compounds:

a) The invention comprises pharmaceutical agents containing one or more compounds of formula I and usual auxiliary agents and vehicles. The invention also comprises pharmaceutical compositions for treatment of a disease, in which the composition comprises a peptide compound of formula I and in which the composition further comprises a pharmacologically acceptable salt and/or a pharmacologically acceptable vehicle.

The peptide compounds according to the invention, their salts and mixtures with pharmacologically harmless vehicles and additives have an effective and long-lasting LHRH-antagonistic action.

The peptide compounds are to be used in the treatment of benign enlargements of the prostate and carcinomas of the prostate. Therefore, the testosterone-reducing potential is tested. For this purpose, generally clearly higher dosages of one and the same antagonists are required than for the induction of an inhibition of ovulation. In the test process used here, intact adult male rats are subcutaneously treated one time with the substance to be tested. The effect on the serum testosterone concentration after 24 hours is determined radioimmunologically (kit of the Biermann company).

The substance of example 13 (point 6.1) induces, in a dosage range of 0.5 to 5 mg/kg of body weight, an inhibition of serum testosterone concentration between 80 and 97% in comparison to the control. Also, in a dosage of 0.25 mg/kg of body weight, an inhibition of 26% is also to be observed.

In addition to the reduction of the testosterone value, the release of histamine is of importance. Thus, edematous changes on the face and/or on the extremities occur at none of the tested dosages (0.1 to 5 mg/kg of body weight subcutaneously), as is typically the case when histamine is released. This in vivo test is ascribed considerably more relevance than the Mastzell test, used in many cases. Nevertheless, the Mastzell test also shows that, with the use of the peptide compound of example 13, the $ED_{50}$ of the release of histamine is still not achieved at 0.01 mg/ml.

Other test processes for the action of LHRH antagonists are i) the inhibition of FSH- and LH-release in rats, which is induced by LHRH. (VILCHEZ - MARTINEZ, J. A. et al. (1975) Endocrinology, 96, 1130) and ii) the inhibition of LH- and FSH-release by distributed, early pituitary cell cultures, as they are tested in the radio-immunoassay test (VALE et al. (1972) Endocrinology 91: 562).

The action of the peptide compounds according to the invention, which has been previously pointed out, results in a number of uses derived from it:

aa) Treatment for benign enlargement of the prostate;

bb) treatment for diseases, which are caused by increased gonad-hormone production in either sex, especially carcinoma of the prostate, cc) treatment of endometriosis, dd) birth control in females, ee) suppression of ovulation or slowing down of ovulation, ff) synchronization of ovulation, hh) estrus suppression, ii) promotion of growth in female animals, kk) induction of menstruation, ll) early abortion in the first three months, mm) treatment of cysts in the breast, nn) treatment of polycystic ovarian syndrome (Stein-Leventhal), oo) birth control in males;

pp) functional castration in male animals in meat production and qq) suppression of menopause symptoms.

Especially preferred is the treatment of carcinomas of the prostate and of endometriosis.

In practice, an effective amount of the peptide compound according to formula 1 or an effective amount of a mixture that contains the peptide compound according to formula 1 and vehicles and/or additives, is administered to humans or animals who or which require such a treatment. The peptide compound or the mixture can be administered by various methods, and the latter can be administered orally, intravenously, subcutaneously, intramuscularly, intravaginally, rectally or nasally. The corresponding method of administration is determined by the form of treatment and by the dosage. Depending on the use, a depot form, an implant or a galenical form slowly releasing the active ingredient can be used.

In the treatment of carcinoma of the prostate in humans (treatment with high doses), daily doses in the range of 1 to 10, preferably 2 to 4 mg per person, are administered.

The exact dosage and the form of administration depends individually on the peptide compound according to formula 1, on the method of administration (path in the blood stream), and on the type and the severity of the conditions to be treated.

b) The invention further comprises a use of a peptide compound according to formula I for use according to one of points aa) to qq). The invention also comprises a use of a peptide compound according to formula I for production of a medicine for therapeutic use according to one of points aa) to qq). Also, the invention relates to a process for use according to one of points aa) to qq) in humans and mammals that require such a use, and the use comprises an administration of a pharmacologically safe and effective amount of the peptide compounds according to formula I in humans and mammals.

c) The invention preferably comprises a use of a peptide compound according to formula I for treatment of carcinoma of the prostate. The invention also comprises a use of a peptide compound according to formula I for the production of a medicine for treatment of carcinoma of the prostate. Also, the invention relates to a process for treatment of carcinoma of the prostate in humans and mammals that require such a treatment, and the treatment comprises an administration of a pharmacologically safe and effective amount of the peptide compounds according to formula I in humans and mammals.

d) The invention preferably comprises a use of a peptide compound according to formula I for treatment of endometriosis. The invention also comprises a use with a peptide compound according to formula I for the production of a medicine for treatment of endometriosis. Also, the invention relates to a process for treatment of endometriosis in humans and mammals that require such a treatment, and the treatment comprises an administration of a pharmacologically safe and effective amount of peptide compounds according to formula I in humans and mammals.

e) The invention preferably comprises a use of a peptide compound according to formula I for birth control. The invention also comprises a use of a peptide compound according to formula I for the production of a medicine for birth control. The invention also relates to a process for birth control in humans and mammals that require such a treatment, and the treatment comprises an administration of a pharmacologically safe and effective amount of the peptide compounds according to formula I in humans and mammals.

Part of the invention is a process for the production of $N^6$-substituted lysine derivatives of general formula XXIV

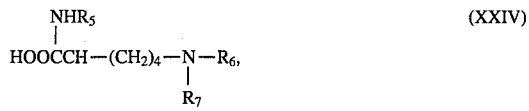

(XXIV)

in which $R_5$ represents a hydrogen atom or an arylsulfonyl radical of general formula XXV

(XXV), with $R_8$ meaning a hydrogen atom or a methyl group and in which $R_6$ and $R_7$ are the same or different and mean at most two hydrogen atoms and/or at most two hydrocarbon radicals, optionally interrupted by at most three oxygen atoms, nitrogen atoms or sulfur atoms and/or substituted at most by two hydroxy groups, cyano groups and/or oxo groups, with up to twelve carbon atoms, characterized in that 3-amino-hexahydro-2-azepinone is reacted in the presence of bases with an arylsulfonyl acid chloride of general formula XXVI

 (XXVI)

in which $R_8$ has the above-mentioned meaning, the formed 3-arylsulfonamidohexahydro-2-azepinone of general formula XXVII

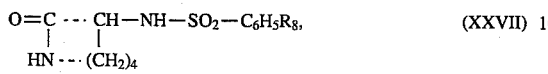 (XXVII)

in which $R_8$ has the above-mentioned meaning, is cleaved by mineral acids to the $N^6$-unsubstituted $N^2$-arylsulfonyl derivative of general formula XXVIII

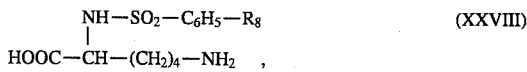 (XXVIII)

in which $R_8$ has the above-mentioned meaning, the latter is optionally N-alkylated or N-acylated to the $N^6$-arylsulfonyl-lysine derivative of general formula XXIX

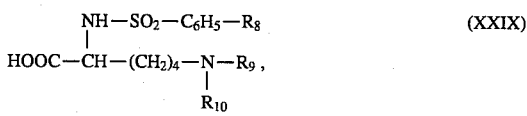 (XXIX)

in which $R_9$ and $R_{10}$ have the same meaning as $R_6$ and $R_7$, provided that at least one of substituents $R_9$ and $R_{10}$ is different from hydrogen and $R_8$ has the above-mentioned meaning, and the latter is optionally converted, by reaction with sodium in ammonia, to the $N^6$-substituted lysine derivative of general formula XXX

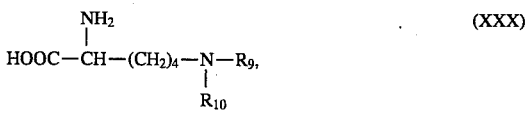 (XXX)

in which $R_9$ and $R_{10}$ have the above-mentioned meaning.

The invention further relates to the $N^6$-substituted $N^2$-arylsulfonyl derivatives of general formula XXIX, in which $R_8$, $R_9$ and $R_{10}$ have the previously mentioned meaning with the exception of $N^6$-benzyloxycarbonyl-$N^2$-tosyl-lysine and $N^6$, $N^6$-dimethyl-$N^2$-tosyl-lysine.

The process according to the invention makes it possible to synthesize these $N^6$-substituted lysine derivatives of general formula XXX in a simple way while achieving good yields. The process according to the invention can be used universally and is suitable to synthesize optically active lysine derivatives of general formula XXX in high purity.

An initial compound for the process according to the invention is 3-amino-hexahydro-2-azepinone (=α-amino-ξ-caprolactam), which is a commercially available preparation both as a racemate and in the form of its optical antipode. This lactam is reacted in the presence of bases with an arylsulfonyl chloride of general formula XXVI (benzenesulfonic acid chloride or preferably p-toluenesulfonic acid chloride) under conditions well-known to one skilled in the art. (Methoden der Organischen Chemie [Methods of Organic Chemistry] (Houben-Weyl); Georg Thieme Verlag, DE-Stuttgart; 4th Edition, Volume XV/1, 1974, page 223). A suitable process is, for example, the reaction of lactam in aqueous phase with an excess of arylsulfonyl chloride in the presence of sodium hydroxide solution.

The corresponding 3-arylsulfonamido-hexahydro-2-azepinone of general formula XXVII, which can be cleaved by mineral acids in a surprising way almost quantitatively to the corresponding $N^2$-arylsulfonyl lysine derivative of general formula XXVIII, is thus obtained. A suitable mineral acid is, for example, aqueous hydrochloric acid up to 12% by weight. The reaction is suitably performed in boiling solution. If optically active 3-arylsulfonamido-2-azepinones are used in this reaction, the corresponding optically active $N^2$-arylsulfonyl lysine derivatives result.

$N^2$-Arylsulfonyl lysine derivatives of general formula XXVIII are already previously known. But they were not used for synthesis of $N^6$-substituted lysine derivatives of general formula XXX, but were used for the production of 3-arylsulfonamidohexahydro-2-azepinones of general formula XXVII (J. Chem. Soc., 1957, 4830–4) or for the production of optically active L-2-piperidyl carboxylic acid (L-pipecolic acid; Bull. Chem. Soc. Japan. 48, 1975, 1341–2).

The $N^2$-arylsulfonyl lysine derivatives of general formula XXIX can be converted to the corresponding $N^2$-arylsulfonyl lysine derivatives of general formula XXIX, by the latter being N-alkylated or N-acylated.

It is obvious to one skilled in the art that $N^6$-substituted $N^2$-arylsulfonyl lysine derivatives as substituents $R_6$ and $R_7$ can contain the most varied groups.

Thus, for example, substituent $R_6$ can be a hydrogen atom. Substituent $R_7$ can be a hydrocarbon radical, optionally interrupted by at most three oxygen atoms, nitrogen atoms or sulfur atoms and/or substituted at most by two hydroxy groups and/or oxy groups, with up to twelve carbon atoms. This hydrocarbon radical can be saturated or unsaturated, as well as alicyclic, cyclic or mixed cyclic. The cyclic or mixed cyclic-alicyclic hydrocarbons can be non-aromatic, aromatic and/or heterocyclic rings systems or contain the latter.

Hydrocarbons that are interrupted by oxygen atoms are, for example, those that contain ether groups (such as the methoxy group, tert-butyloxy group or the benzyloxy group). Such ethers can optionally be used to synthesize substances that contain hydroxy groups. Other hydrocarbons that are interrupted by oxygen atoms, are, for example, those that contain furan rings, tetrahydrofuran rings, pyran rings or 1,3-dioxolan rings. The latter can optionally be used to synthesize substances that contain carbonyl groups.

Hydrocarbons that are substituted by oxo groups are, for example, those that are bonded by a carbonyl group to the $N^6$-amino group of the lysine, i.e., amides. On the other hand, such hydrocarbons are also those that contain amide groups or carbonyloxy groups.

Hydrocarbons that are interrupted by nitrogen atoms are, for example, those that contain dialkylamino groups, such as dimethylamino groups, pyrrolino groups (Houben-Weyl, 4th Edition, Volume XVII, 1974, page 293) or dibenzylamino groups.

The radicals of this type also include aromatic N-heterocycles or hydrocarbons that contain such N-heterocycles.

Hydrocarbon radicals that are interrupted by sulfur atoms are, for example, thioether and those hydrocarbons that contain thiophene rings.

On the other hand, the $N^6$-substituted $N^2$-arylsulfonyl lysine derivatives of general formula XXIX, as substituents $R_9$ and $R_{10}$, can also have two of the above-mentioned organic radicals. These radicals can be the same or different. Further, the two radicals $R_9$ and $R_{10}$ together can mean a hydrocarbon radical optionally interrupted by oxygen atoms, nitrogen atoms or sulfur atoms and/or substituted by hydroxy groups and/or oxo groups and thus form, together with the nitrogen atom, a preferably five- to seven-membered heterocycle, which for its part can be substituted again in the previously described way.

$N^6$-substituted $N^2$-arylsulfonyl lysine derivatives of general formula XXIX are, for example, those of general formula XXXI

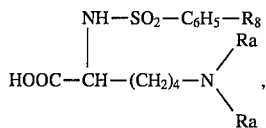
(XXXI)

in which $R_8$ has the above-mentioned meaning and the two radicals Ra, in each case, symbolize alkyl groups with up to 4 carbon atoms. These compounds can be produced, for example, from the $N^6$-substituted compounds of general formula XXVIII by reaction with alkyl bromides or alkyl iodides under the known conditions (Houben-Weyl, 4th Edition, Volume XI/1, 1957, p. 24 ff). If it is desired to produce N,N-dimethyl compounds of general formula XXXI (Ra=CH$_3$), this can be done advantageously by reductively alkylating the $N^6$-unsubstituted compound with formaldehyde and catalytically activated hydrogen or with formaldehyde in the presence of formic acid (Houben-Weyl, 4th Edition, Volume XI/2, 1958, p. 330 and 331).

$N^6$-Substituted $N^2$-arylsulfonyl lysine derivatives of general formula XXIX are further those of general formula XXXII

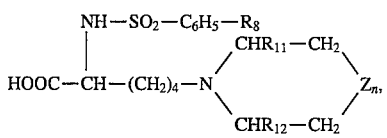
(XXXII)

in which $R_8$ has the above-mentioned meaning, $R_{11}$ and $R_{12}$ are the same or different and mean a hydrogen atom, a cyano group, an alkyl group with at most 6-carbon atoms, a phenyl group or pyridyl group optionally substituted by 1 to 3 alkyl groups with at most 4 carbon atoms or 1 to 3 alkoxy groups with at most 4 carbon atoms, and in which $Z_n$ symbolizes a carbon-carbon bond, a methylene group, an oxygen atom or a sulfur atom.

Such compounds are, for example, those that are substituted in 6-position by a pyrrolidino group, a 3-pyridinyl-pyrrolidino group, a piperidino group, a morpholino group, a 3-cyanomorpholino group or a 1,4-tetrahydrothiazino group.

These compounds can be produced by reductive alkylation from the corresponding dicarbonyl compounds of general formula XXXIII

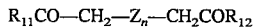
(XXXIII), in which $R_{11}$, $R_{12}$ and $Z_n$ have the above-mentioned meaning, and from $N^6$-unsubstituted $N^2$-arylsulfonyl lysine derivatives, by these components being reacted with metal hydrides, sodium borohydride or, advantageously, sodium cyanoborohydride. (Synthesis 1975, 135–146; J. Amer. Chem. 29, 1986, 1225–1230, J. Org. Chem. 28, 1963, 3259–3261).

Thus, this reductive alkylation can be performed, for example, by the sodium cyanoborohydride being allowed to act at room temperature on the components in a polar—preferably hydrous—inert solvent, such as hexanemethylphosphoric acid triamide, acetonitrile, etc. or in water itself at a pH of 6 to 8.

$N^6$-substituted $N^2$-arylsulfonyl lysine derivatives of general formula XXIX worth mentioning are also those of general formula XXXIV

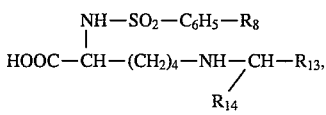
(XXXIV)

in which $R_8$ has the above-mentioned meaning and in which $R_{13}$ and $R_{14}$ together with the —CH group form a 5- and/or 6-membered isocyclic ring system or in which $R_{13}$ symbolizes an alkyl radical with up to 6 carbon atoms or a phenyl radical or pyridyl radical optionally substituted by 1 to 3 alkyl groups with up to 4 carbon atoms or by 1 to 3 alkoxy groups with up to 4 carbon atoms, and $R^{14}$ [sic] has the same meaning as $R_{13}$ or represents a hydrogen atom.

Such compounds, for example, are a compound of general formula XXXIV, substituted in 6-position by an alkylamino group—such as, for example, a methylamino group, ethylamino group, propylamino group, isopropylamino group, butylamino group, tert-butylamino group, a cycloalkylamino group, such as the cyclopentylamino group, a 2-adamatylamino group or a 1-phenylethylamino group.

These compounds can also be produced by reductive alkylation from the corresponding carbonyl compounds of general formula XXXV

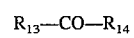
(XXXV), in which $R_{13}$ and $R_{14}$ have the above-mentioned meaning, and from $N^6$-unsubstituted $N^2$-arylsulfonyl lysine derivatives, by the components being reacted under the already mentioned conditions either with metal hydrides, such as sodium borohydride or sodium cyanoborohydride, or catalytically activated hydrogen.

This can happen, for example, by the components being reacted in a polar solvent, such as ethyl acetate, with sodium borohydride at room temperature.

As $N^6$-substituted $N^2$-arylsulfonyl lysine derivatives of general formula XXIV, there are, finally, also $N^6$-acylated compounds of general formula XXXVI

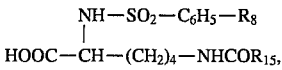
(XXXVI)

in which $R_8$ has the above-mentioned meaning and $R_{15}$ represents the radical of a carboxylic acid $R_{15}$COOH with at most 12 carbon atoms.

Such radicals $R_{15}$ are, for example, alkyl groups with up to 6 carbon atoms, such as the methyl group, the ethyl group, the propyl group, the isopropyl group, the butyl group or the tert-butyl group, cyclopentyl group or the cyclohexyl group, cycloalkylalkyl groups, such as the cyclopentylmethyl group or the 2-cyclopropyl-ethyl group or phenyl radicals, 1- or 2-naphthyl radicals or pyridyl radicals optionally substituted by hydroxy groups, 1 to 3 alkyl groups with up to 4 carbon atoms or 1 to 3 alkoxy groups with up to 4 carbon atoms.

These amides are synthesized from the corresponding reactive derivatives of carboxylic acids, such as, for example, acid chlorides or acid anhydrides, by methods that are well-known to one skilled in the art. (Houben-Weyl, Volume XV/1, 1974).

The sulfonic acid group can be cleaved from the $N^6$-substituted $N^2$-arylsulfonyl lysine derivatives of general formula XXIX. This happens suitably by reaction with sodium in boiling ammonia (Houben-Weyl, Volume XV/1, 1974, p. 228 ff), and the 6-substituted lysine derivatives of general formula XXX are achieved in good yields and with good optical purity.

This is surprising to one skilled in the art since it is generally known "that the relatively complicated elimination of N-tosyl masking, achievable only in drastic conditions and seldom free of side reactions, leads more and more to disregard the use of this protective group—also for the blocking of the ω-amino or the guanido function—in favor of other radicals" (Houben-Weyl, Volume XV/1, 1974, p. 241).

Further, the invention comprises a process for the production of an amino acid derivative according to the invention, in which an N-α-protected ω-amino-α-amino acid is reacted with a dialdehyde in the presence of a reducing agent and then the protective group is cleaved.

The invention also comprises a process for the production of a peptide compound according to the invention by using known amino acid derivatives and at least one amino acid derivative according to the invention, by the amino acid derivatives being condensed in a homogeneous phase or according to the solid-phase method,
in which a) the carboxyl end of an amino acid derivative to be coupled, whose amino groups and optionally functional groups of the side chain carry a protective group, reacts with the free amino end of the amino acid derivative to be coupled or of the peptide fragment to be coupled in the presence of a condensation reagent,
and b) then the α-amino protective group of the coupled amino acid derivative is cleaved
and
optionally other amino acid derivatives are coupled to the peptide chain to be synthesized after the previously described two steps and, after coupling of the last amino acid in the case of the solid-phase method, the peptide compound from the solid phase is cleaved.

The following embodiments are used to explain the process according to the invention in more detail.

General Synthesis of the Peptides

The peptides of the invention can be produced by techniques that are known to on-the-spot experts in the field of peptide synthesis. A summary of many of these techniques can be looked up in J. M. STEWART and J. D. YOUNG, San Francisco, 1969, and J. MEIENHOFER, Hormonal Proteins and Peptides, Vol. 2, p. 46, Academic Press (New York), 1973 for the solid-phase method and E. SCHRODER and K. Lubke, The Peptides, Vol. 1, Academic Press (New York) 1965 for the liquid-phase method. The steps of the synthesis are described in EP-OS 0 097 031.

The general process steps of the European laid-open specification can be applied analogously to the synthesis of the peptide compounds according to the invention described here.

Specially represented, the peptides according to the invention can be produced as follows:

The peptides are constituted by steps on a benzhydrylamine resin containing about 0.5 m equivalents of $NH_2$/g on an ACT synthesizer, after beginning with FMOC-D-Ala according to described processes.

The couplings are performed according to diagram A as follows:

DIAGRAM A

Reagent
1. FMOC-amino acid (2 to 3 mmol/g of resin)
2. 4 equivalents of hydroxybenzotriazole-hydrate calculated based on amino acids used
3. 4 equivalents of BOP-reagent
4. 4 equivalents of diisopropylethylamine N, N-Dimethylformamide is used as solvent. The coupling time is about 30 minutes.

The deblocking is performed according to Diagram B:

DIAGRAM B

5. Flushing with dimethylformamide (twice)
6. 20% piperidine in dimethylformamide, 3 times in 3 minutes
7. flushing with dimethylformamide (twice)

In summary, the FMOC is used to protect the α-amino groups. tBu is used as a protective group for the hydroxy group of the Ser and the phenolic hydroxy group of the Tyr. The Mtr group is used to protect the guanido functions of the Arg.

To cleave the protected peptide resin and to leave it unprotected, it is treated with trifluoroacetic acid over a period of at least one hour. The trifluoroacetic acid is separated from undissolved resin and evaporated to dryness in a vacuum. The desired peptide is isolated in pure form from the residue by preparative HPLC according to known processes.

EXAMPLES 1.1. Production of 5-(1-aza-cycloalk-1-yl)-2-acetamido-2-ethoxycarbonyl-pentanoic acid ethyl ester
(General instructions)

First 10 ml of benzene and 1 mmol of sodium methoxide are added to 5.0 g (23 mmol) of acetamidomalonester. Then, 23 mmol of acrolein is instilled over 30 minutes, and by outer cooling with ice water, it is provided that the reaction temperature does not exceed +35° C. It is stirred for 60 more minutes (and the temperature increases to about +10° C.) and adjusted with acetic acid to pH 7 (moistened indicator paper). The reaction solution is concentrated by evaporation in a vacuum and the oily residue is dissolved in 20 ml of methanol (dried by molecular sieve, 4 angstroms).

It is cooled again with ice water and 23 mmol of azacycloalkane, 46 mmol of sodium acetate, 2.5 g of molecular sieve (4 angstroms) and finally 46 mmol of sodium cyanoborohydride are added in succession. After completion of the gas generation, it is stirred for 16 hours at +20° C. It is adjusted with aqueous sodium carbonate solution to pH 10, extracted three times with 100 ml of ethyl acetate each, the organic phases are combined, extracted with saturated sodium chloride solution, dried on sodium sulfate and the filtrate is concentrated by evaporation.

1.2. Production of three special pentanoic acid ethyl esters
1.2.1. Example 1: Production of 5-(morpholin-4-yl)-2-acetamido- 2-ethoxy-carbonyl-pentanoic acid ethyl ester:

Starting from 21.7 g of acetamidomalonester, 34.5 g of crude product is obtained, from which, after silica gel chromatography (dichloromethane, methanol 95:5; v/v), 12.8 g of pure product (oil) is obtained.
1.2.2. Example 2: Production of 5-(pyrrolidin-1-yl)-2-acetamido- 2-ethoxycarbonyl-pentanoic acid ethyl ester:

Starting from 5.0 g of acetamidomalonester, 6.6 g of crude product is obtained, which is further reacted without further purification.
1.2.3. Example 3: Production of 5-(thiomorpholin-4-yl)-2-acetamido- 2-ethoxycarbonyl-pentanoic acid ethyl ester:

Starting from 5.0 g of acetamidomalonester, 7.5 g of crude product is obtained, from which, after silica gel chromatography (dichloromethane, methanol 95:5; v/v), the pure product is obtained.

2. Production of 6-bromo-2-acetamido-2-ethoxycarbonyl-hexanoic acid ethyl ester (Example 4)

The mixture of 86.9 g of acetamidomalonester, 215.9 g of 1,4-dibromobutane, 4 g of triethyl-benzyl-ammonium-chloride, 82.8 g of potassium carbonate and 400 ml of acetonitrile is refluxed for 24 hours. The undissolved components are filtered off on Celite, the filtrate is concentrated by evaporation in a vacuum and the residue is concentrated by evaporation in a vacuum three times with 500 ml of water each. The residue is digested with 500 ml of diethyl ether and allowed to stand overnight at +5° C. The filtrate from the undissolved elements is concentrated by evaporation in a vacuum. The residue is purified by silica gel chromatography (tert-butyl-methyl ether, hexane; 7:3; v/v). 64 g of pure product is obtained.

Melting point: 61°–62° C.

3.1. Production of 6-(1-aza-cycloalk-1-yl)-2-acetamido-2-ethoxycarbonyl-hexanoic acid ethyl ester (General instructions)

352 mg of 6-bromo-2-acetamido-2-ethoxycarbonyl-hexanoic acid ethyl ester (cf. Example 4) is added to the solution of 2 ml of aza-cycloalkane in 2 ml of diethyl ether and stirred for 12 hours at 20° C. The reaction solution is concentrated by evaporation in a vacuum and the residue is mixed with 10 ml of water. After extraction three times with 10 ml of ethyl acetate each, the organic phases are combined and dried on sodium sulfate. The filtrate is concentrated by evaporation in a vacuum.

3.2. Production of several special hexanoic acid ethyl esters 3.2.1. Example 5: Production of 6-(morpholin-4-yl)-2-acetamido- 2-ethoxy-carbonyl-hexanoic acid ethyl ester:

Starting from 70 g of 6-bromo-2-acetamido-2-ethoxycarbonylhexanoic acid ethyl ester, after reaction with morpholine and silica gel chromatography (dichloromethane, methanol/gradient: 0 on 10% methanol; v/v), 35 g of pure product is obtained.

Melting point: 58°–59° C.

3.2.2. Example 6: Production of 6-(pyrrolidin-1-yl)-2-acetamido- 2-ethoxycarbonyl-hexanoic acid ethyl ester:

Starting from 352 mg of 6-bromo-2-acetamido-2-ethoxycarbonyl-hexanoic acid ethyl ester, after reaction with pyrrolidine and silica gel chromatography (dichloromethane, methanol 7:3; v/v), 251 mg of pure product is obtained.

Melting point: 79°–81° C.

3.2.3. Example 7: Production of 6-(1-methyl-piperazin-4-yl)-2-acetamido- 2-ethoxycarbonyl-hexanoic acid ethyl ester:

Starting from 352 mg of 6-bromo-2-acetamido-2-ethoxycarbonyl-hexanoic acid ethyl ester, after reaction with 1-methyl-piperazine and silica gel chromatography (dichloromethane, methanol 7:3; v/v), the pure product is obtained.

3.2.4. Example 8: Production of 6-(piperidin-1-yl)-2-acetamido- 2-ethoxy-carbonyl-hexanoic acid ethyl ester Starting from 352 mg of 6-bromo-2-acetamido-2-ethoxycarbonyl-hexanoic acid ethyl ester, after reaction with piperidine and silica gel chromatography (dichloromethane, methanol 7:3; v/v), 148 mg of pure product is obtained.

Melting point: 73°–75° C.

3.2.5. Example 9: Production of 6-(imidazole)-2-acetamido-2-ethoxycarbonyl-hexanoic acid ethyl ester:

Starting from 352 mg of 6-bromo-2-acetamido-2-ethoxycarbonyl-hexanoic acid ethyl ester, after reaction with imidazole and silica gel chromatography (dichloromethane, methanol/gradient: 0 on 10% methanol; v/v), the pure product is obtained.

3.2.6. Example 10: production of 6-(pyrazole)-2-acetamido-2-ethoxycarbonyl-hexanoic acid ethyl ester:

Starting from 352 mg of 6-bromo-2-acetamido-2-ethoxycarbonyl-hexanoic acid ethyl ester, after reaction with pyrazole and silica gel chromatography (dichloromethane, methanol 7:3; v/v), the pure product is obtained.

4. Production of (S)-6-(thiomorpholine-1,1-dioxid-4-yl)-2-aminohexanoic acid (Example 12):

4.1. Production of (S)-6-amino-2-benzyloxycarbonylamino-hexanoic acid benzyl ester (Z-Lys-OBzl)

The compound was produced according to the known process; e.g.: E. Wünsch, in: "Methoden der Organischen Chemie [Methods of Organic Chemistry]," Vol XV/1: "Synthese von Peptiden [Synthesis of Peptides]" (Georg Thieme Verlag, 1974), B. Bezas, L. Zervas; J. Am. Chem. Soc. 83, 719 (1961).

4.2. (S)-6-(Thiomorpholine-1,1-dioxid-4-yl)-2-benzyloxycarbonylamino-hexanoic acid benzyl ester:

5.6 g of Z-Lys-OBzl is dissolved in a mixture of 750 ml of methanol and 750 ml of dichloromethane. After adding 1.8 g of divinyl sulfone, it is stirred for 6 hours at +20° C. The solvent is distilled off in a vacuum and the residue is purified chromatographically on silica gel (gradient 0 to 10% ethyl acetate/tert-butyl-methyl ether). Yield: 1.8 g (oil).

4.3. (S)-6-(Thiomorpholine-1,1-dioxid-4-yl)-2-amino-hexanoic acid

The cleavage of the protective groups is performed according to a known process: e.g.: E. Wünsch, in: "Methoden der Organischen Chemie, Volume XV/1: Synthese von Peptiden" (Georg Thieme Verlag, 1974).

5. Conversion of (1-aza-cycloalk-1-yl)-2-acetamido-2-ethoxycarbonyl-pentanoic acid- or -hexanoic acid ethyl ester to the corresponding unprotected α-amino acids.

The above-mentioned precursor stages, which exist as an enantiomer mixture corresponding to the production process, are saponified according to processes that are well-known to the chemist, first partially to (1-aza-cycloalk-1-yl)-2-acetamido-2-carboxy-pentanoic acid- or -hexanoic acid ethyl esters and then decarboxylated to (1-aza-cycloalkyl-1-yl)-2-acetamido-pentanoic acid or hexanoic acid. After enzymatic racemate separation, the enantiomer-pure amino acids are obtained by total hydrolysis.

The processes were described, for example, by:

C. K. Acosta et al.; J. Chem. Research (M) 11, 914–934 (1991)

K. Folkers et al.; Int. J. Pept. Prot. Res. 24, 197–200 (1984)

6. Production of Peptides

The peptides can be produced either according to the solid-phase technique or according to the standard solution technique.

The solid-phase technique is described, e.g., in J. M. STEWARD and J. D. YOUNG, Solid Phase Peptide Synthesis, Pierce Chem. Company, Rockford, Ill. 1984, the solution technique is represented, e.g., in Methoden der Organischen Chemie (HOUBEN/WEYL), Vol. 15/No. 1 and 2, E. WUNSCH (Editors), Thieme Verlag Stuttgart, 1974.

The common feature of all these syntheses is the blocking of the α-amino group and the optionally present reactive side chain groups so that the α-amino group can be selectively released. This strategy allows an activation and selective reaction of the carboxyl group of the N-protected amino acid with the free α-amino group of a second amino acid. After completion of the coupling, the α-amino protective group can be cleaved and the next coupling can be made. In the case of solid-phase synthesis, the C-terminal carboxyl group is bonded to the carrier resin, with which solution method it can be protected by a suitable group. With both methods, instead of the individual amino acids, suitable peptide fragments can also be linked. According to both methods, a polypeptide with protected or partially protected side chain functions is obtained. After cleavage of the protective groups, the desired peptide can be obtained pure by HPLC.

Examples 13 to 15

As examples for the peptide compound, three decapeptides are indicated, whose production was previously described. The properties of the three decapeptides are listed in tabular form. The legends for the abbreviations are located after Example 15.

6.1. Example 13

7.1. Example 16

Production of D-3-tosylamidohexahydro-2-azepinone 18 g of D-3-amino-hexahydro-2-azepinone is dissolved in 180 ml of water and mixed with 5.6 g of finely granulated sodium hydroxide and 29.5 g of tosyl chloride. The suspension is vigorously stirred. As soon as the pH decreases, it is adjusted with sodium hydroxide to pH=9. The mixture is stirred overnight, the separated product is filtered off, washed with water and crystallized or digested from hot methanol. 25.5 g of D-3-tosylamido-hexahydro-2-azepinone with melting point 213° C. is obtained.

$[\alpha]_d^{23}$ −120.8°.

7.2. Example 17

Production of $N^2$-tosyl-D-lysine-hydrochloride

A suspension of 14.8 g of D-3-tosylamidohexahydro-2-azepinone in 1.2 l of 12% hydrochloric acid is refluxed for

| Ac—D—Nal—D—Cpa—D—Pal—Ser—Tyr—D—Cit—Leu—Ahx(Mor)—Pro—D—Ala—NH₂ | | | | | | | | | | |
|---|---|---|---|---|---|---|---|---|---|---|
| | D—Nal | D—Cpa | D—Pal | Ser | Tyr | D—Cit | Leu | Ahx(Mor) | Pro | D—Ala |
| ASA cld | 1.00 | 1.00 | 1.00 | 1.00 | 1.00 | 1.00 | 1.00 | 1.00 | 1.00 | 1.00 |
| ASA[a)] fnd | 1.03 | 0.98 | 1.01 | 0.95 | 0.97 | 1.03 | 1.01 | 0.96 | 1.00 | 0.97 |
| RAC[b)] | <1 | 1.2 | 2.5 | <1 | <1 | c) | <1 | c) | 1.1 | 1.3 |

FAB-MS molecular peak m/e 1472.6 (+H). Calculated molecular weight 1473.1

The peptide compound of Example 13 is the preferred embodiment, 6.2. Example 14

1.5 to 2 hours until a clear solution results. Then, the solution is evaporated to dryness in a vacuum. The residue is digested with hot hexane/isopropanol, the white crystals are suctioned off, so that the filtrate is somewhat concentrated by evaporation and brought to −20° C. for further crystalliza-

| Ac—D—Nal—D—Cpa—D—Pal—Ser—Tyr—D—Ahx(Mor)—Leu—Arg—Pro—D—Ala—NH₂ | | | | | | | | | | |
|---|---|---|---|---|---|---|---|---|---|---|
| | D—Nal | D—Cpa | D—Pal | Ser | Tyr | D—Ahx(Mor) | Leu | Arg | Pro | D—Ala |
| ASA cld | 1.00 | 1.00 | 1.00 | 1.00 | 1.00 | 1.00 | 1.00 | 1.00 | 1.00 | 1.00 |
| ASA[a)] fnd | 1.05 | 1.02 | 1.03 | 0.95 | 0.96 | 0.97 | 1.00 | 0.96 | 0.98 | 0.95 |
| RAC[b)] | <1 | 1.6 | 3.3 | <1 | 0.8 | 1.0 | <1 | <1 | <1 | 1.3 |

FAB-MS molecular peak m/e 1471.9 (+H), Calculated molecular weight 1472.2

6.3. Example 15 tion. 15.1 g of $N^2$-tosyl-D-lysine-hydrochloride with melting point 189° C. is obtained.

$[\alpha]_d^{23}$ = −2.18°.

| Ac—D—Nal—D—Cpa—D—Pal—Ser—Tyr—D—Ahx(Mor)—Leu—Ahx(Mor)—Pro—D—Ala—NH₂ | | | | | | | | | |
|---|---|---|---|---|---|---|---|---|---|
| | D—Nal | D—Cpa | D—Pal | Ser | Tyr | D—Ahx(Mor) | Leu | Pro | D—Ala |
| ASA cld | 1.00 | 1.00 | 1.00 | 1.00 | 1.00 | 2.00 | 1.00 | 1.00 | 1.00 |
| ASA[a)] fnd | 1.05 | 1.01 | 1.01 | 0.95 | 0.95 | 1.93 | 0.97 | 0.98 | 0.96 |
| RAC[b)] | 1.6 | 1.5 | 2.6 | <1 | 0.8 | d) | <1 | <1 | 1.1 |

FAB-MS molecular peak m/e 1513.8 (+H), Calculated molecular weight 1514.2 a) ASA=amino acid analysis of the hydrolyzate.

Hydrolysis conditions: 6M HCl solution, 110° C. 24 hours.

b) RAC=portion of the undesired enantiomers in percent. Determination according to H. Frank, G. J. Nicholson and E. Bayer, J. Chromatogr. Science 15, 174 (1977).

c) The determination is not possible, since the tested Cit- and Ahx(Mor) derivatives exhibit the same gas-chromatographic retention times.

d) The ratio of D-Ahx(Mor): L-Ahx(Mor) is 1:1.

7. Production of $N^6$-substituted lysine derivatives 7.3. Example 18

Production of 2,2'-oxybis-(acetylaldehyde)

25 g of 1,4-anhydromeso-erythite is dissolved in 400 ml of water. Then, 41.1 g of solid sodium periodate is added to the solution with ice cooling, the mixture is stirred overnight and adjusted with solid sodium bicarbonate to pH 7.4. It is mixed with 400 ml of acetonitrile, the inorganic salts are filtered off and a solution of 2,2'-oxybis(acetaldehyde) is obtained.

7.4. Example 19

Production of $N^2$-tosyl-6-(morpholin-1-yl)-2-D-aminohexanoic acid.

37.8 g of $N^2$-tosyl-D-lysine is dissolved in 22 l of tridistilled water and the solution is adjusted to pH 7.4 with sodium bicarbonate. Then, 14.1 g of sodium cyanoborohydride is added and the freshly prepared 2,2'-oxy-bis(acetaldehyde) solution. The reaction mixture is stored for 12 days at room temperature and then concentrated by evaporation in a vacuum in portions. The residue is dried in a high vacuum, taken up in absolute methanol/dichloromethane (1+1), the inorganic salts are filtered off and the obtained crude product is roughly chromatographed by a silica gel column by absolute methanol/dichloromethane 1+1.

25.6 g of $N^2$-tosyl-6-(morpholin-1-yl)-2-D-aminohexanoic acid as crude material with a decomposition point starting from 120° C. is thus obtained.

$[\alpha]_D^{23} = -9.3°$ (water c=1).

7.5. Example 20

Production of 6-(morpholin-1-yl)-2-D-aminohexanoic acid 16.8 g of $N^2$-tosyl-6-(morpholin-1-yl)-2-D-aminohexanoic acid is dissolved at −70° C. in 500 ml of liquid ammonia (dried on potassium hydroxide) and then mixed at −40° C. to −33° C. with small sodium particles for at least 3 minutes Until an intensive blue coloring occurs. Then, the solution is decolored by adding some drops of acetic acid and the ammonia is allowed to evaporate overnight. The obtained residue has the ammonia residues removed in a high vacuum, it is taken up in tridistilled water and adjusted with diluted hydrochloric acid to pH 4. The amino acid is absorbed in a strongly acidic ion exchanger, the latter is washed in a column with 3% hydrochloric acid and water, and the compound is eluted with 3n aqueous ammonia. The solvent is drawn off in a vacuum and subsequent high vacuum, and 8.7 g of 6-(morpholin-1-yl)-2-D-aminohexanoic acid is obtained, which is digested in a little methanol/dichloromethane. Melting point above 325° C.

$[\alpha]_D^{23} = 22.3°$ (c=1 6n hydrochloric acid).

Enantiomer excess 100%.

7.6. Example 21

Production of $N^6$-isopropyl-$N^2$-tosyl-D-lysine 2 g of N-tosyl-D-lysine-hydrochloride is mixed with 5 ml of glacial acetic acid, 1.5 g of anhydrous sodium acetate, 10 ml of water and 5 ml of acetone. Then, enough glacial acetic acid is added with stirring that a clear solution results. The mixture is cooled to 0° C. and a total of 2 g of sodium borohydride is added with stirring in small portions. Then, 5 ml of acetone is again added and a total of 2 g of sodium borohydride is again added in small portions.

The obtained suspension is concentrated by evaporation in a vacuum and then in a high vacuum, the residue is dissolved in hot methanol. With cooling to 10° C., 1.2 g of $N^6$-isopropyl-$N^2$-tosyl-D-lysine crystallizes out.

White needles of melting point 251° C.

$[\alpha]_D^{23} = +11.29°$

Additional amounts of the compound can be obtained from the mother liquors by crystallization.

7.7. Example 22

Production of $N^6$-isopropyl-D-lysine

Under the conditions of the example under 7.5., 342 mg of $N^6$-isopropyl-$N^2$-tosyl-D-lysine is reacted. 170 mg of $N^6$-isopropyl-D-lysine with melting point 224° C. is obtained.

$[\alpha]_D^{23} = 18.9°$ (c=1; 6n hydrochloric acid)

Enantiomer excess 98.6%.

We claim:

1. A peptide of formula I

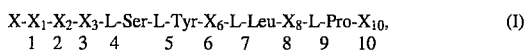

wherein

X is a naphthoyl, naphthylacetyl, naphthylpropionyl, benzoyl group or a $C_{1-7}$-acyl group;

$X_1$ is D-(1)-Nal, D-(2)-Nal, D-Phe, D-(4-Y)-Phe, D-(3)-Qal or a direct bond;

$X_2$ is D-Phe, D-(4-Y)-Phe or a direct bond;

$X_3$ is D-Trp, D-Phe, D-(4-Y)-Phe, D-(3)-Pal, D-(2)-Nal or a direct bond;

Y is F, Br or Cl;

$X_6$ is D-Cit, D-Hci, D-Orn, D-Lys or D-Neu, and $X_8$ is L-Orn, L-Arg, L-Lys or L-Neu, and at least one of radicals $X_6$ and $X_8$ is respectfully, D-Neu or L-Neu;

$X_{10}$ is D-Ala-$NH_2$, Gly-$NH_2$, azaglycine, —NHEt or —NH(CO)$NH_2$, and

Neu is (a) a group of formula II,

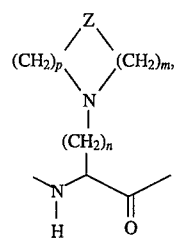

wherein Z is

>$CH_2$, >C=O, >CH(OH), >O, >S, >S=O, >$SO_2$, >$NR_1$ or >N(CO)$R_2$, wherein $R_1$ is H or a $C_1$-$C_4$-alkyl group and $R_2$ is H, a $C_1$-$C_4$-alkyl group or an amino group;

n is 1 to 8;

m is 1 to 3, if Z is one of radicals —($CH_2$)—, —CO— or —CH(OH)—, or m is 2 or 3, if Z is one of radicals —O—, —S—, —SO—, —$SO_2$—, —$NR_1$— or —N(CO)$R_2$—;

p is 1 to 3;

or (b) a group of formula IV,

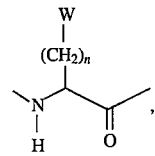

wherein W is

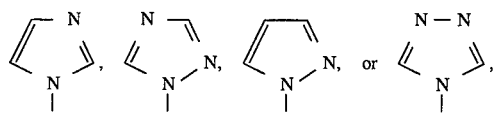

and n is 1 to 8.

2. A peptide of claim 1, wherein Neu is a radical of formula IX

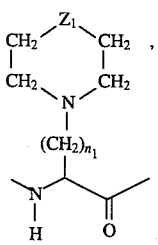 (IX)

wherein $Z_1$ is

>$CH_2$, >CH(OH), >O, >S, >$SO_2$, >$NCH_3$, or a direct bond, and $n_1$ is 3 to 6.

3. A peptide of claim 2, wherein Neu is a group of formula X

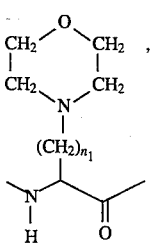 (X)

wherein $n_1$ is 3 to 6.

4. A peptide of claim 3, wherein Neu is

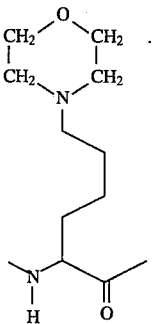

5. A peptide of claim 4, wherein $X_6$ or $X_8$ is Neu.

6. A peptide of claim 1, wherein Neu is a group of formula XIII

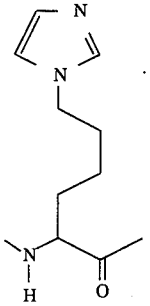 (XIII)

7. A peptide of claim 1 wherein

X is an ethanoyl group, $X_1$ is D-Nal, $X_2$ is D-Cpa, $X_3$ is D-Pal, and $X_{10}$ is D-Ala-$NH_2$.

8. A pharmaceutical composition comprising an effective amount of a peptide of claim 1 and a pharmaceutically acceptable excipient.

* * * * *